United States Patent [19]

Bart

[11] Patent Number: 4,736,088
[45] Date of Patent: Apr. 5, 1988

[54] THERAPEUTIC HEATING PAD AND MUFF STRUCTURE

[75] Inventor: Gordon B. Bart, Sturgis, Mich.

[73] Assignee: Battle Creek Equipment Company, Battle Creek, Mich.

[21] Appl. No.: 756,273

[22] Filed: Jul. 18, 1985

[51] Int. Cl.$^4$ ............................ H05B 1/00; H05B 3/34
[52] U.S. Cl. .................... 219/211; 219/529; 219/527; 128/379; 128/402
[58] Field of Search ............ 219/211, 527-529, 219/545; 128/379, 381, 399, 402

[56] References Cited

U.S. PATENT DOCUMENTS

| | | | |
|---|---|---|---|
| 1,142,393 | 6/1915 | Bloomer | 219/529 |
| 2,590,212 | 3/1952 | Samuels | 219/527 X |
| 2,769,892 | 11/1956 | Collins | 219/527 |
| 3,130,289 | 4/1964 | Katzman et al. | 219/528 X |
| 3,178,559 | 4/1965 | Fogel et al. | 219/528 X |
| 4,107,509 | 8/1978 | Scher et al. | 219/527 X |
| 4,245,149 | 1/1981 | Fairlie | 219/528 |
| 4,279,255 | 7/1981 | Hoffman | 219/528 X |
| 4,303,074 | 12/1981 | Bender | 219/528 |
| 4,310,745 | 1/1982 | Bender | 219/548 X |
| 4,518,851 | 5/1985 | Oppitz | 219/528 X |

*Primary Examiner*—E. A. Goldberg
*Assistant Examiner*—C. M. Sigda
*Attorney, Agent, or Firm*—Irvin L. Groh; Alfred L. Patmore, Jr.

[57] ABSTRACT

A therapeutic heating pad having a laminate structure which concentrates the flow of heat in one direction through the laminate including a flannel lamina in contact with a body member being treated to produce a moist hot heat to foment the body member. The laminate structure is adaptable to be held in a tubular configuration to form a muff for fomentation of a body member inserted therein.

4 Claims, 3 Drawing Sheets

THERAPEUTIC HEATING PAD AND MUFF STRUCTURE

This invention relates to electric heating pads, and, more particularly, to a therapeutic heating pad which produces a hot moist heat which acts as a fomentation to the body member to which it is applied. In one embodiment the therapeutic pad is constructed or held in a tubular configuration to form a muff into which the body member is inserted for treatment.

The prior art discloses a variety of heating pads showing various heating element constructions arranged to provide uniform heating, flexibility and the like. These pads in general are used at low heats, many providing a four position selector switch or a continuous setting potentiometer to obtain a comfortable, pleasing heat for the user.

The Underwriter's Laboratories and other testing companies set forth various standards for materials, construction and testing of heating pads. For example, the 1983 edition of the American National Standards Institute/Underwriter's Laboratories Standard known as ANSI/UL 130 contains 33 pages of such standards including product marking. One of the items to which a lot of attention has been directed is the maximum temperature that the pad obtains, dictating, on one hand, laboratory standards for testing the reliability of thermostats, and requiring, on the other hand, innovation on the part of the designer in properly locating these thermostats.

U.S. Pat. No. 2,215,042 shows a common known spiral arrangement for the resistance wire which is covered with an asbestos insulation and stitched to a backing; the designer here has put metal sheets on both sides of the heating element to conduct heat to the thermostat. In U.S. Pat. No. 3,119,926 the heating element is in the form of two side by side sinuous coils extending from one end of the pad to the other with nine thermostats evenly dispersed about the pad. U.S. Pat. Nos. 2,154,184 and RE 29,641 both utilize a heating element composed of several rows of small backward and foreward sinuous loops providing flexibility; the first patent showing the use of a four position switch, and the other patent showing a thermostat placement for fast response.

While U.S. Pat. No. 2,154,184 recognizes that higher heats are desirable for therapeutic treatments, the patentee alternatively providing a spring action switch for such treatments, and U.S. Pat. No. RE 29,641 recognizes the therapeutic value of a moist heat and provides a heating pad which applies moist heat without the need of wetting the pad, there appears to be no teaching of further developing the combination of high heat concentration applied to a sheet capable of retaining moisture to create a hot moist heat providing a fomentation to a body member to which the pad is applied.

Examples of efforts to supply a moist heat by the use of a conventional heating pad structure in combination with a removable sponge-like pad which is saturated with water or water based medicant are shown in U.S. Pat. No. 2,590,212 where the water pad is slipped into a pocket of the outer slipcover of the heating pad, and U.S. Pat. No. 4,107,509 where a saturated sponge is inserted into a heating muff.

It is an object of this invention to provide a therapeutic heating pad structure having a moisture retaining material for application to a body member to be treated and a uniform source of intense heat acting against the material to provide hot moist heat as a fomentation.

It is another object of this invention to provide a more efficient use of a given heat density, usually defined in terms of watts per square inch of heating pad surface, to provide rapid heating and release of water vapor from a natural moisture containing material.

It is a further object of this invention to provide a therapeutic heating pad in which the heat generated by a heating element lamina is constrained to flow in one direction relative to and through the laminate to uniformly heat a moisture containing flannel lamina producing a moist heat fomenting the body member to which the pad is applied.

Another objective is to provide a flexible heating pad laminate which is adaptable to be held in a tubular configuration to serve as a therapeutic heating muff into which a body member can be inserted for fomentation treatment.

A still further objective is to provide a therapeutic heating muff which is adjustable so that its effective diameter can be reduced or enlarged to accommodate body members inserted therein such as the hands, or an elbow or knee joint, to provide hot moist fomentation to such body member.

The foregoing objectives and inherent purposes are served in a therapeutic heating pad for applying moist hot heat as a fomentation to a body member wherein the pad has a laminate structure having the following serially juxtapositioned laminas; a fabric serving as a decorative and protective outer cover; a batting preferably of a polyester material serving as a heat insulating barrier; a metallic foil, preferably in the form of a flexible foil-fabric composite; a flexible electrical heating element; a vapor barrier preferably in the form of a vinyl sheet; and a flannel moisture pervious sheet which inherently is hygroscopic or hydrophilic in nature to retain moisture gathered from the atmosphere so that when the laminate pad is applied to a body member, the heat generated by the heating element lamina is confined against flow in one direction relative to and through the laminate by the batting and the fabric laminas and is directed by the foil lamina in the opposite direction towards the body member to uniformly heat the flannel lamina through the vapor lamina producing a moist heat, fomenting said body member.

In the manufacture of the therapeuric pad laminate the fabric lamina is chosen to be both decorative and to have durability, having a pattern color and meeting the usual flammability test. The batting lamina is preferably a polyester batting, also meeting the flammability standard and serving the primary service of heat insulation. The foil lamina is in the form of a flexible foil-cloth laminate meeting burn tests. These three layers are quilted together to form a unitary base, which effectively retards flow of heat therethrough from the foil-cloth composite toward the fabric cover.

The heating element lamina is in the form of an insulated electrical resistance wire, preferably nichrome covered with a silicone rubber covering which is mounted on the quilted base on the face of the reflective foil in a continuous, winding path taking the form of a sinuous curve from edge to edge of the base sheet. Two spaced thermostats are placed in series with the resistance wire, and the heating element lamina is held to the foil lamina by an adhesive glass tape. The heating element lamina thus forms a heat source of substantially uniform heat density over the area of the pad.

The vapor barrier lamina is preferably a vinyl sheer which completely covers the heating element lamina and is sewn to the quilted base.

Finally, the flannel moisture pervious sheet lamina provides a hygroscopic or hydrophilic media which is placed in contact with the body member receiving the therapeutic treatment. This flannel lamina is detachably connected to the pad structure by any suitable means such as snaps or Velcro hook and loop fastener strips attached to the edges of the vapor barrier lamina and the flannel lamina. This provides a body contact lamina which may be laundered as required.

The pad structure can be provided with means for holding the laminate in a tubular configuration to form a muff with the flannel lamina innermost for fomentation treatment of body members inserted therein. The holding means conveniently takes the form of adjustable straps which are mounted to the fabric. A strap is mounted at each parallel edge of the structure and at the mid point with one end of the strap overlapping the fabric so that adjustment may be made to reduce or enlarge the effective diameter of the muff to accommodate the body member. Typically, the muff serves for treatment of arthritic conditions in the hands of the user. The muff structure can also be conveniently used to provide therapeutic treatment for arm and leg members such as the elbow or knee joints of the user.

In the preferred embodiment, the strap members have one of a hook and loop fastening surface facing inward, and a cooperating strip with the other of a hook and loop fastening surface which is mounted on the fabric lamina facing outward and in line with the straps to engage a selected portion of the strap determining the effective diameter of the muff.

Preferably, when the laminate structure is formed into a muff, the flannel lamina is also sewn to form a tubular lining and is detachably connected to the inside of the muff along its outer edges by Velcro hook and loop strips thereby preventing accidental insertion of a body member between the flannel and vapor barrier laminas.

The presently preferred embodiments of the invention are illustrated in the accompanying drawing in which.

Figure 1:
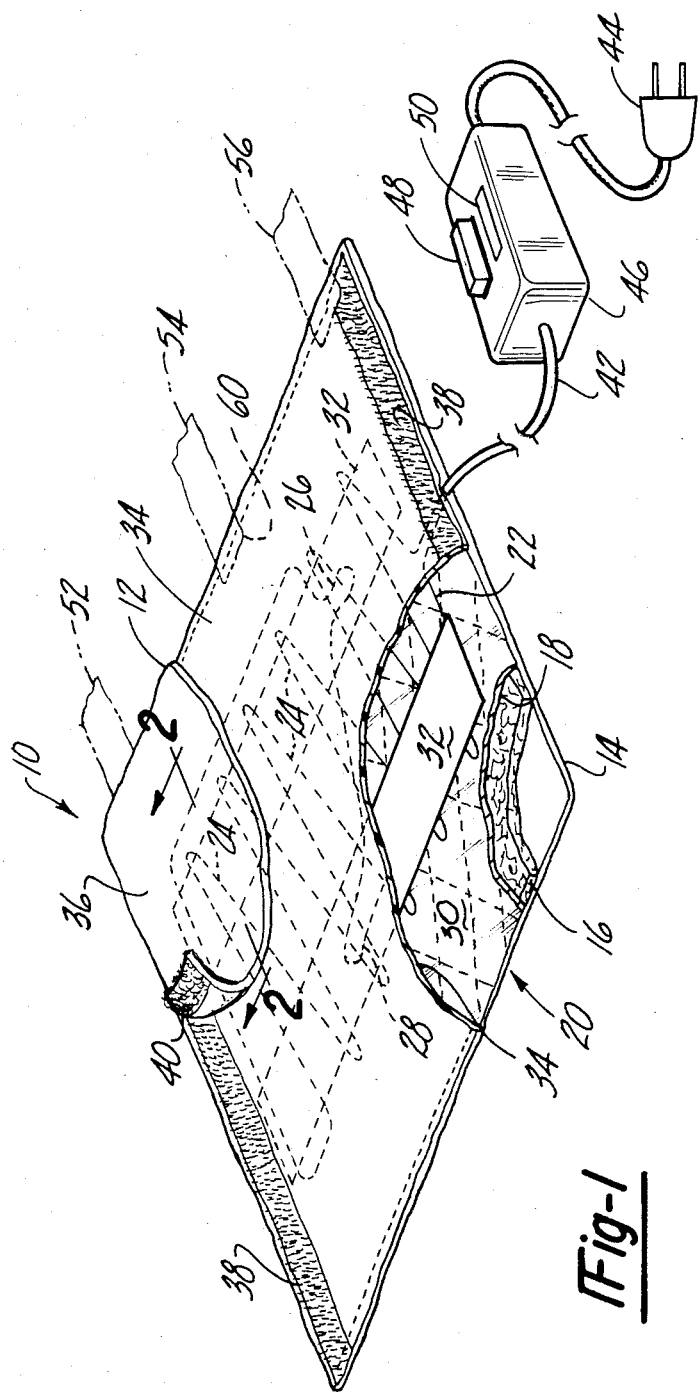
FIG. 1 is a perspective view of the laminate structure broken away to reveal the details of the individual laminas embodied in the subject invention.
Figure 2:
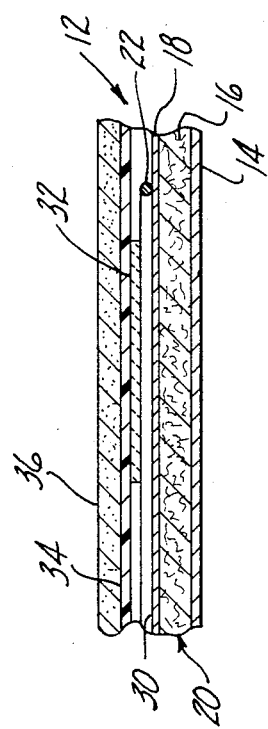
FIG. 2 is a cross-sectional view taken along line 2—2 of FIG. 1 further identifying the individual laminas of the laminate structure embodying the invention.

The therapeutic pad 10 according to the invention is constructed in a laminate form from individual rectangular shaped lamina sheets. Contrary to most conventional heating pad constructions, the laminate structure of this invention is not a symmetrical construction with a central heating element surrounded by one or more envelopes so that the heat radiates from both faces. The construction of laminate 12 has been specifically designed to restrict flow through the laminas in one direction and convey heat flow through the laminas in the other direction toward the body member to which the pad has been applied.

Fabric lamina 14 is a decorative cloth having a colored pattern design with good wear qualities for durability. Fabric 14 serves as the outer cover of the pad 10. The serially next lamina is batting 16 formed from a material meeting flammability specifications and preferably is manufactured from a polyester material. The primary purpose of batting lamina 16 is to act as a thermal insulation barrier. The serially next lamina is a metallic foil 18 which serves as a reflector surface. The metallic foil is preferably formed as a foil-cloth composite retaining all of the heat reflective properties on one side but adding all the advantages of a fabric as the foil is deeply imbedded into the fabric providing a flexible and durable composite. Such a foil-cloth or foil-fabric product is sold under the Trade name, FABRIFOIL, manufactured by the Duracote Corporation.

I have found that a stable unitary based structure can be formed for mounting of the electrical element lamina by quilting the fabric, batting, and foil-cloth laminas together forming quilted base 20.

The electric heating element lamina takes the form of a resistance wire mounted on the metallic foil surface of the foil-cloth lamina in a winding path to provide a substantially uniform heat density. The wire can conventionally be of a nickel iron chrome alloy such as nichrome of a suitable diameter to provide the proper relationship between total heat or wattage output for the given area of the heating element lamina. Typically, a nichrome wire of 0.008–0.010 inches when constructed in the form of a zigzag coil with approximately two inch spacings between adjacent legs or coil turns 24 and layed out on a 12 to 16 inch width span and a number of coils to cover a length of approximately 16 inches will produce the desired heat density for the pad. Typically, the wattage rating of most pads is something less than 0.40 watts per square inch of pad area. I prefer to construct my heating element lamina with a wattage rating of approximately 0.5 watts per square inch to provide the proper fomentation action as set forth below. Spaced thermostat units 26 and 28 are mounted in series with resistance wire 22 to perform the well known safety function of shutting the pad off at a given upper temperature limit. Both thermostats 26 and 28 are set at the same upper limit. This upper limit may vary between 60° C. and 95° C. depending the area of the pad and the particular standard to which the pad has been tested, as well known in the art. I prefer a temperature setting at the high end of the scale to assure fast moisture release for fomentation. The coil turns 24 and thermostats 26 and 28 are held affixed to the reflective foil surface 30 of the foil-cloth lamina 18 by the use of glass tape strips 32.

Vapor barrier lamina 34 covers the electric element lamina 22 and is stitched to quilted base 20 along the edges as shown at 36. Vapor barrier 34 is preferably made from vinyl sheeting.

The final lamina of the pad laminate construction is flannel moisture pervious sheet 36 which is detachably connected to the quilted base 20 over vapor barrier 34 by suitable fastening means located along the edges of the pad. Preferably this connection is by way of Velcro hook and loop fastening strips with one of the cooperating strips located along the edges of the quilted base over vapor barrier lamina 34 and the other strip located around the edges of the flannel lamina 36. As shown in FIG. 1, the Velcro hook strip 38 is fastened to the quilted base 20 and the Velcro loop strip 40 is sewn to the edges of the flannel lamina. This provides an easy detachable connection for the flannel sheet to be removed for laundering.

Electric power is supplied to the resistance element 22 by electric line cord 42 fitted with line plug 44 and switch unit 46. Switch unit 46 preferably contains a spring-loaded switch 48 which must be depressed and be kept in the depressed condition in order to supply power to the pad. This type of spring-loaded switch provides protection to the user requiring his hand pressure to keep the power supplied to the pad. Amber indicating light 50 indicates when power is being supplied to the pad.

In use, pad 10 is applied to the body portion requiring treatment with the flannel sheet lamina against the patient's or user's skin. The flannel being a natural hygroscopic or hydrophilic material attracts and retains moisture from the atmosphere so that when the switch 48 is depressed supplying power to the electrical element lamina 22, heat is reflected by foil surface 30 of foil-cloth lamina 18 through vapor barrier lamina 34 to rapidly heat flannel sheet lamina 36 releasing hot moisture as a fomentation to the body part. Heat flow in the opposite direction is resisted not only by reflection in the other direction by foil surface 30, but also by the batting lamina 16 and fabric lamina 14, which act as heat insulators confining the heat flow in the other direction toward the patient's body member. This greatly enhances the total heat flow toward the flannel, body contacting lamina over conventional heating pads in which heat flow is unrestricted in both directions from the pad surfaces.

The combination of the high density heating amplified by the reflective foil surface 30 and the moisture retention by vapor barrier 34 assures a hot moist fomentation.

Figure 3:
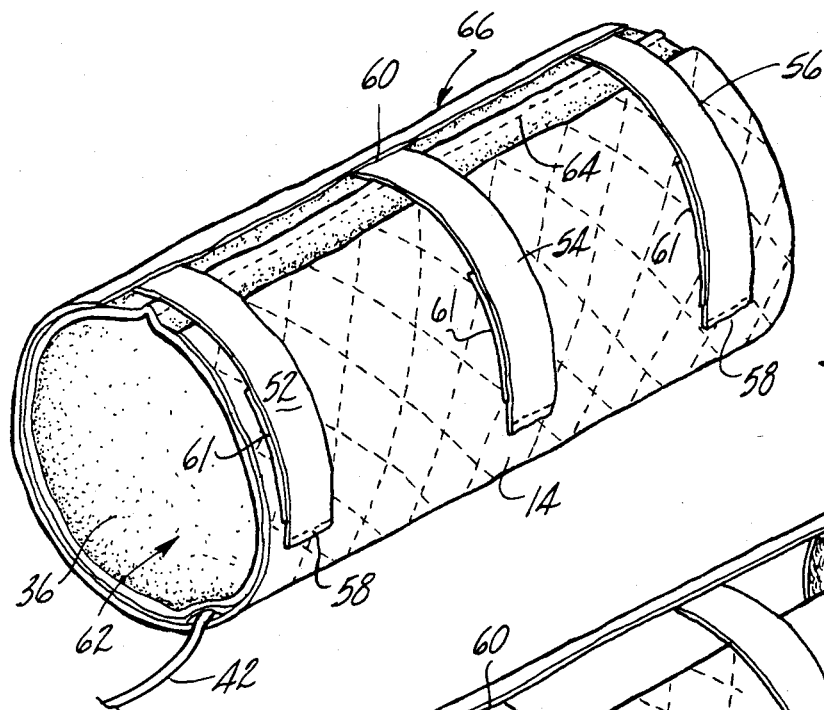
FIG. 3 is a perspective view of the laminate structure embodying the invention held in a tubular configuration forming a therapeutic muff into which the body members to be treated are inserted.
Figure 4:
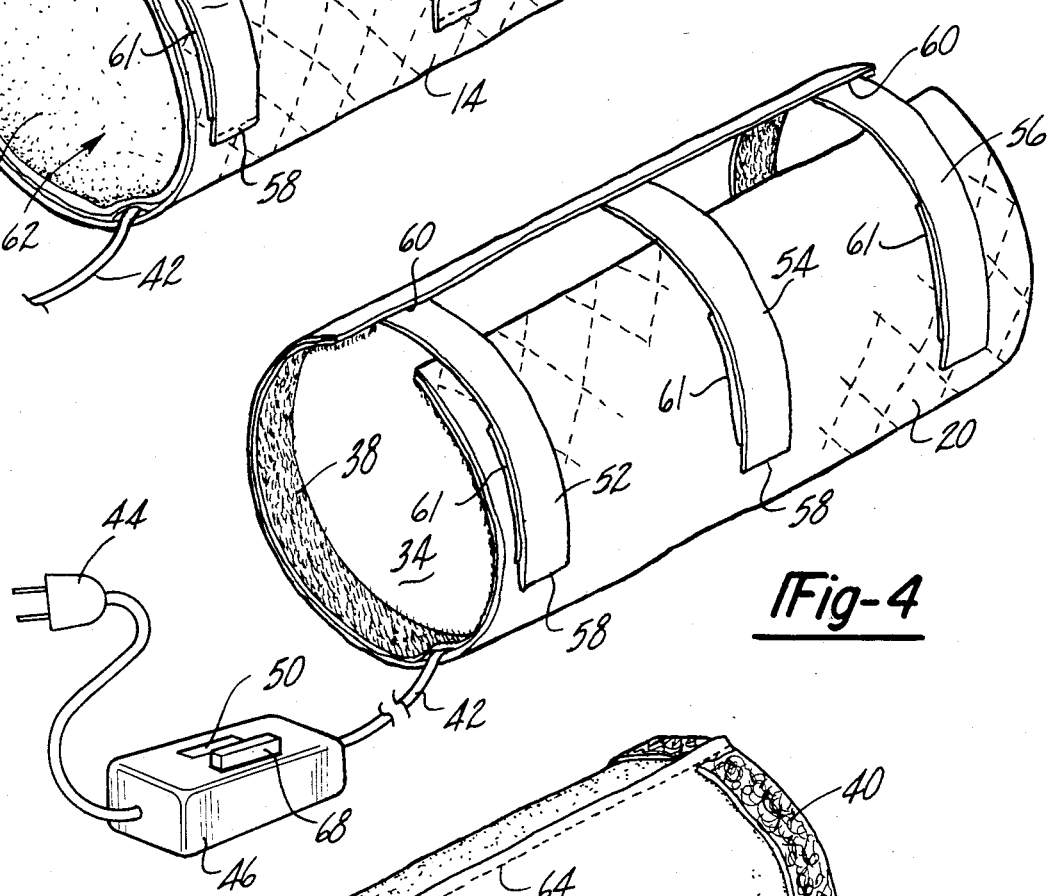
FIG. 4 is a perspective view similar to FIG. 3 showing the muff structure of the invention with the flannel liner lamina removed.
Figure 6:
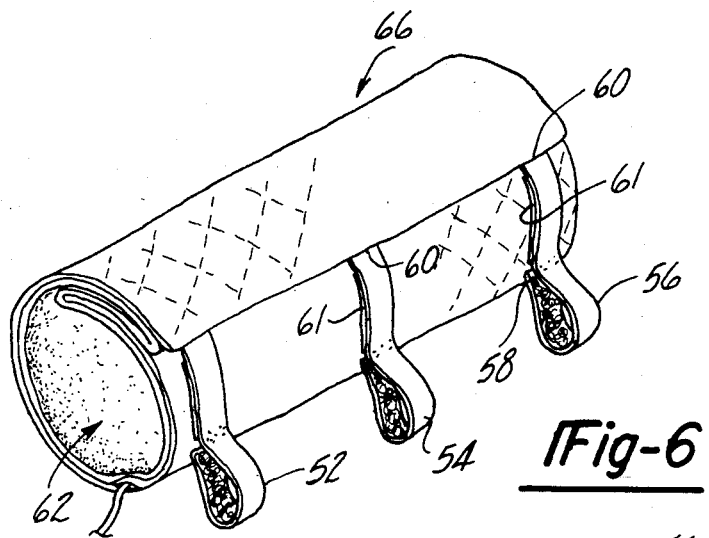
FIG. 6 is a view similar to FIG. 3 on a smaller scale showing the straps in an adjusted position providing the minimum diameter of the muff.

The flexible unitary construction of laminate 12 makes it ideally suited for adaptation to a heating muff configuration by the provision of holding straps 52, 54 and 56, which hold pad 12 in a tubular configuration. Straps 52 and 56 are attached parallel to and adjacent the edges of the pad, and strap 54 is located intermediate straps 52 and 56. Adjustable straps 52, 54 and 56 are attached at one of their ends 58 as by sewing to the face of fabric 14. The other end of straps 52, 54 and 56 are attached to the quilted base 20 adjacent one end thereof as by sewing, shown at 60. Straps 52, 54 and 56 have one of a hook and loop fastening surface facing inward, shown as a Velcro loop connector, with the other of the hook and loop fastening surface strip 61 being attached to the fabric lamina facing outward and in line with the straps adjacent to stitching 58 so as to engage a selected portion of the strap determining the effective diameter of the muff. The strips 61 are shown as Velcro hook fasteners. FIG. 3 shows the straps 52, 54 and 56 attached to strips 61 adjacent ends 58 to provide the largest muff diameter. FIG. 6 shows the straps in an engagement to produce the minumum diameter of the muff 66.

In the muff configuration, the flannel lamina 36 is preformed into a tubular liner configuration 62 as by stitching along seam 64.

Figure 5:
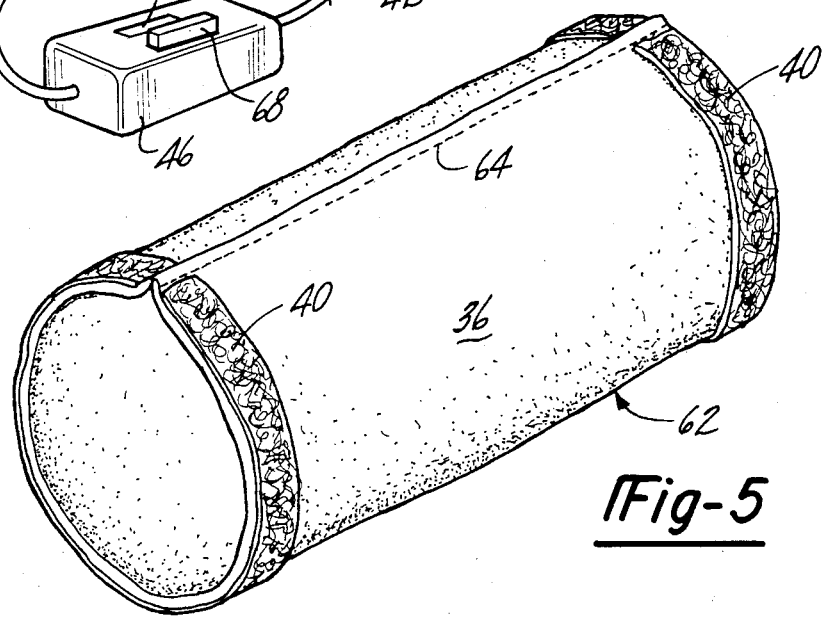
FIG. 5 is a perspective view of the flannel lamina of the muff sewn into a tubular lining.

As shown at FIG. 5, the Velcro loop strips 40 are stitched to liner 62 adjacent each edge with no need for a similar strip to be affixed along seam 64. When the therapeutic heating pad 10 is formed as a heating muff 66 it is particularly advantageous to have these Velcro fastening strips 38 and 40 be continuous along the entire edge of the pad to prevent the user from inserting his hand between the flannel liner 62 and the vapor barrier lamina 34.

With the muff configuration 66, it is more convenient to provide switch unit 46 with an on/off push button switch 68 instead of the spring-loaded switch 48 due to the fact that the muff will be used to a large extent for the fomentation treatment of arthritic finger joints where the hands are inserted within the muff and cannot retain the spring-loaded switch in the on position.

Figure 7:
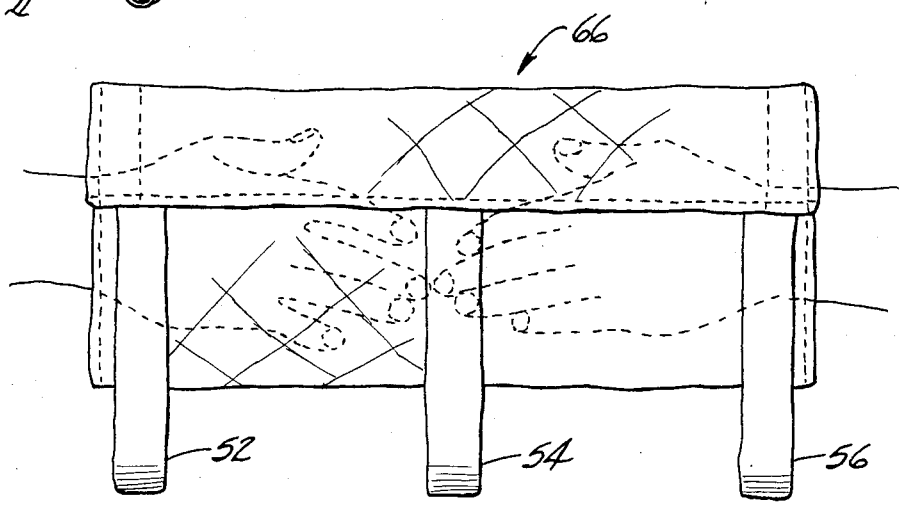
FIG. 7 is a partial sectional view of the muff showing the user's hands inserted therein.
Figure 8:
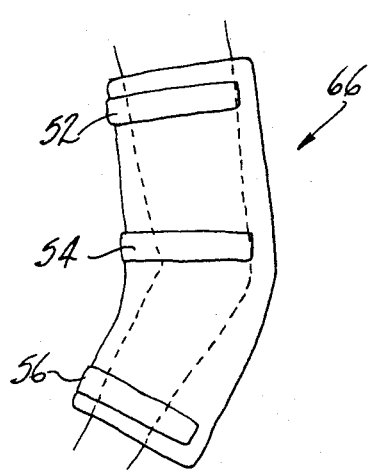
FIG. 8 is a schematic representation of the muff with an arm member inserted therein for treatment of the elbow joint.
Figure 9:
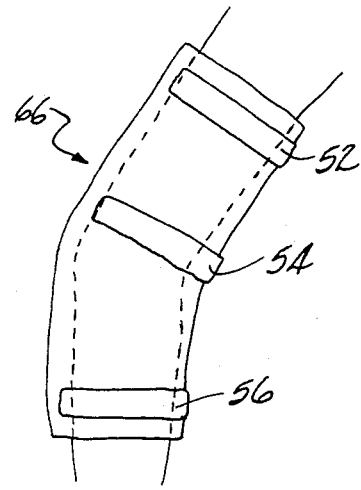
FIG. 9 is a view similar to FIG. 8 showing treatment of a knee joint.

In use, straps 52, 54 and 56 are loosened to provide the maximum diameter for insertion of the body member such as the arm or elbow treatment shown in FIG. 8, and the leg or knee treatment shown in FIG. 9. Once the muff has been properly positioned, the user or an attendant will adjust the straps 52, 54 and 56 to snugly seal the muff against the body member. When the hands are to be inserted, as shown in FIG. 7, the straps 52, 54 and 56 will be adjusted by trial before final insertion of the hands within the muff. Likewise, switch 68 will be turned on before the hands are inserted in the muff.

The extremely efficient flow of heat inward from the heating element lamina 22 and reflected from the metal foil surface 30 through the vapor barrier 34, heating and releasing moisture from the flannel liner 62, provides a very effective fomentation of the body member inserted in the muff. With the concentrarion of heat radially inward, the thermostat units 26 and 28 can be set at the lower end of the spectrum, for example, at 60° C., while still maintaining the high moisture release rate produced from the high watt density of the heating element lamina 22.

The embodiments of the invention in which an exclusive property or privilege is claimed are defined as follows:

1. A therapeutic heating pad held in a muff for applying moist heat as a fomentation to a body member inserted therein, said muff comprising a four sided rectangular laminate structure having the following serially juxtapositioned laminas and construction:

a fabric, an insulating padding and foil-cloth composite laminas quilted together to form a base sheet;

a flexible electrical heating element and a vapor barrier lamina in combination with said base sheet completing said rectangular structure;

a pair of adjustable straps each affixed adjacent their ends to said structure positioned parallel and adjacent to two sides of said structure, one end of each strap overlapping said fabric lamina, holding said structure in a tubular muff configuration adjustable to reduce and enlarge the effective diameter of the muff by adjustment of said straps to accomodate a body member; and a flannel moisture pervious liner formed in a tubular configuration detachably connected within said muff along each edge thereof;

whereby heat generated by said heating element lamina is confined against outward flow through the lamina from said muff by said batting and fabric laminas and is directed by said foil-cloth composite lamina inwardly to uniformly heat said flannel liner through said vapor barrier lamina producing a moist heat fomenting said body member inserted within said muff.

2. The heating muff of claim 1 further comprising a third adjustable strap parallel to and between said pair of adjustable straps.

3. The heating muff according to claim 2 wherein said straps have one of a hook and loop fastening surfaces facing inwardly and extending along the length of the straps, and further comprising cooperating strips with the other of said hook and loop fastening surfaces mounted on said fabric lamina adjacent to the ends of said straps affixed to the fabric lamina facing outwardly in line with said straps to engage a selective portion of each strap determining the effective diameter of said muff.

4. The heating muff according to claim 1 wherein said flannel liner is detachably connected by cooperating hook and loop fastening strips attached along the sides of said liner and said vapor barrier lamina.

* * * * *